(12) United States Patent
Dreyfuss

(10) Patent No.: US 8,591,592 B2
(45) Date of Patent: Nov. 26, 2013

(54) METHOD OF IMPLANTING PARTIAL HUMERAL HEAD PROSTHESIS

(75) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 376 days.

(21) Appl. No.: 12/113,849

(22) Filed: May 1, 2008

(65) Prior Publication Data
US 2008/0306601 A1 Dec. 11, 2008

Related U.S. Application Data

(60) Provisional application No. 60/915,280, filed on May 1, 2007.

(51) Int. Cl.
| | | |
|---|---|---|
| A61F 2/40 | (2006.01) | |
| A61B 17/32 | (2006.01) | |
| A61B 17/58 | (2006.01) | |
| A61B 17/88 | (2006.01) | |
| A61B 17/16 | (2006.01) | |
| A61B 17/17 | (2006.01) | |
| A61B 17/90 | (2006.01) | |

(52) U.S. Cl.
USPC .......... 623/19.14; 606/80; 606/301; 606/304; 606/104; 606/99; 606/96; 623/908

(58) Field of Classification Search
USPC .......... 623/19.11–19.14; 606/79–81
See application file for complete search history.

(56) References Cited

U.S. PATENT DOCUMENTS

| 4,484,570 | A | * | 11/1984 | Sutter et al. | 606/282 |
|---|---|---|---|---|---|
| 5,100,405 | A | * | 3/1992 | McLaren | 606/304 |
| 5,409,332 | A | * | 4/1995 | Chabot et al. | 403/114 |
| 2001/0012967 | A1 | * | 8/2001 | Mosseri | 623/23.12 |
| 2002/0022889 | A1 | | 2/2002 | Chibrac et al. | |
| 2003/0014123 | A1 | | 1/2003 | Copf et al. | |
| 2005/0043805 | A1 | * | 2/2005 | Chudik | 623/19.14 |
| 2005/0154398 | A1 | * | 7/2005 | Miniaci et al. | 606/96 |
| 2005/0159751 | A1 | * | 7/2005 | Berthusen et al. | 606/80 |
| 2006/0085006 | A1 | * | 4/2006 | Ek et al. | 606/86 |

FOREIGN PATENT DOCUMENTS

| EP | 1 260 200 A | 11/2002 |
|---|---|---|
| EP | 1 407 728 A | 4/2004 |
| FR | 2 578 739 A | 9/1986 |
| WO | WO 97/47257 | 12/1997 |

* cited by examiner

*Primary Examiner* — Marcia Hoffman
(74) *Attorney, Agent, or Firm* — Dickstein Shapiro LLP

(57) ABSTRACT

A humeral prosthesis includes a stem component and a partial humeral head component. The partial humeral head component has a configuration that is similar to the curvature of the humeral head to allow the head to reconstruct the anatomy of the damaged humerus. The stem component is threaded and cannulated and engages the partial humeral head component. The stem component is configured to be inserted within the humeral diaphyseal channel.

6 Claims, 16 Drawing Sheets

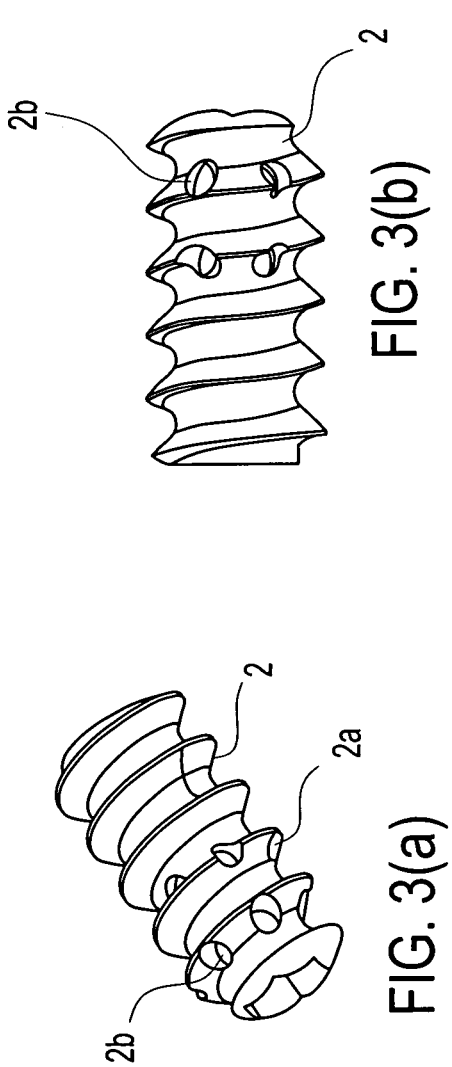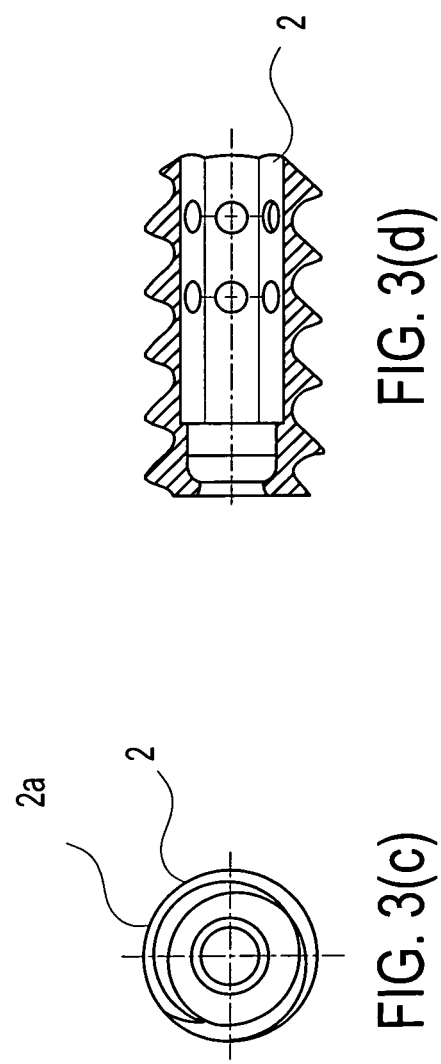

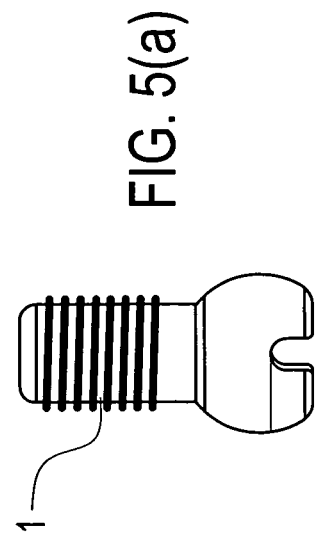
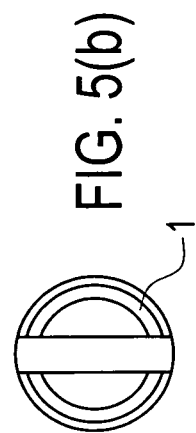
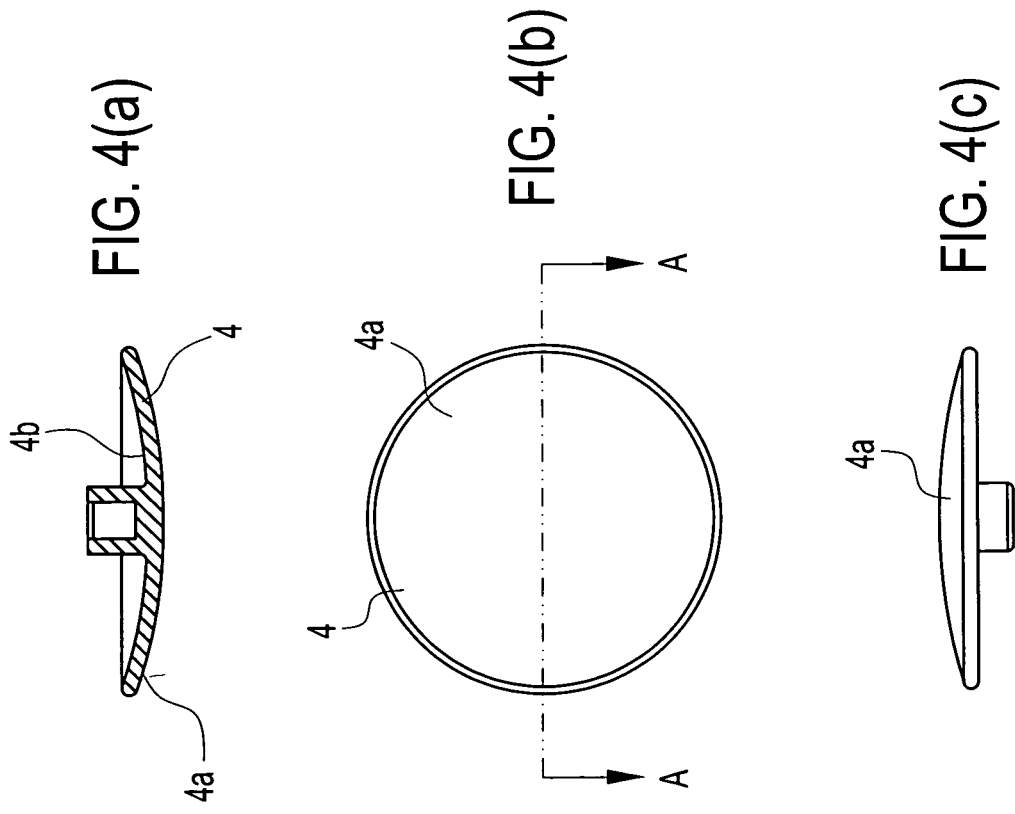

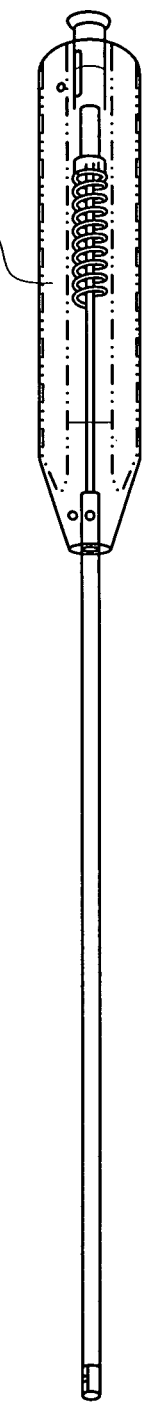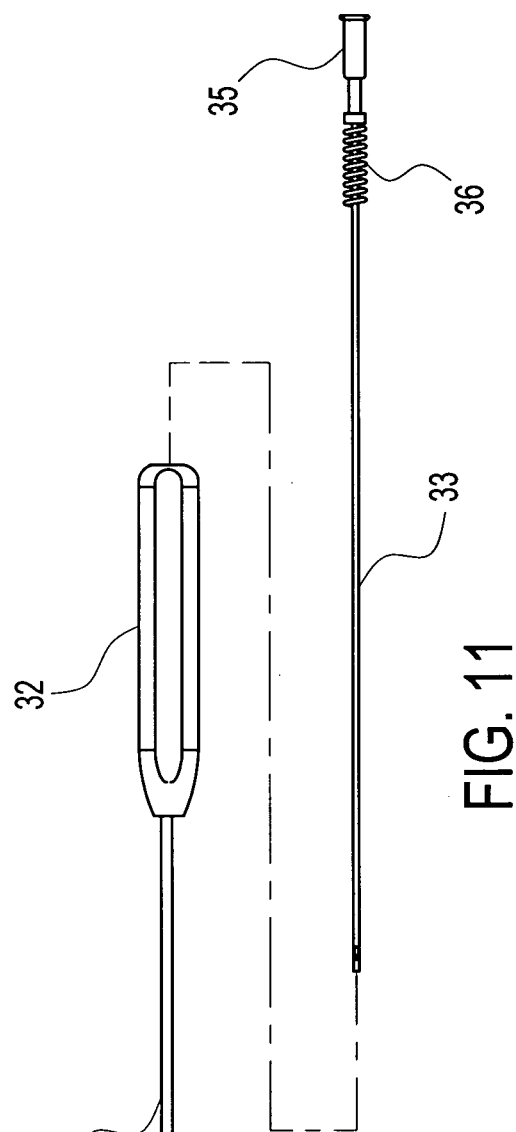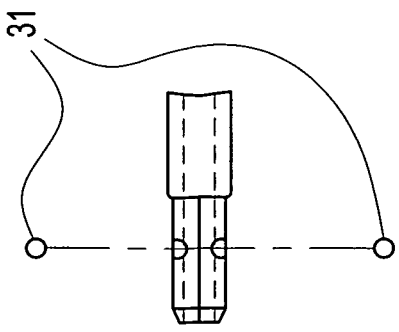
FIG. 9
FIG. 10
FIG. 11

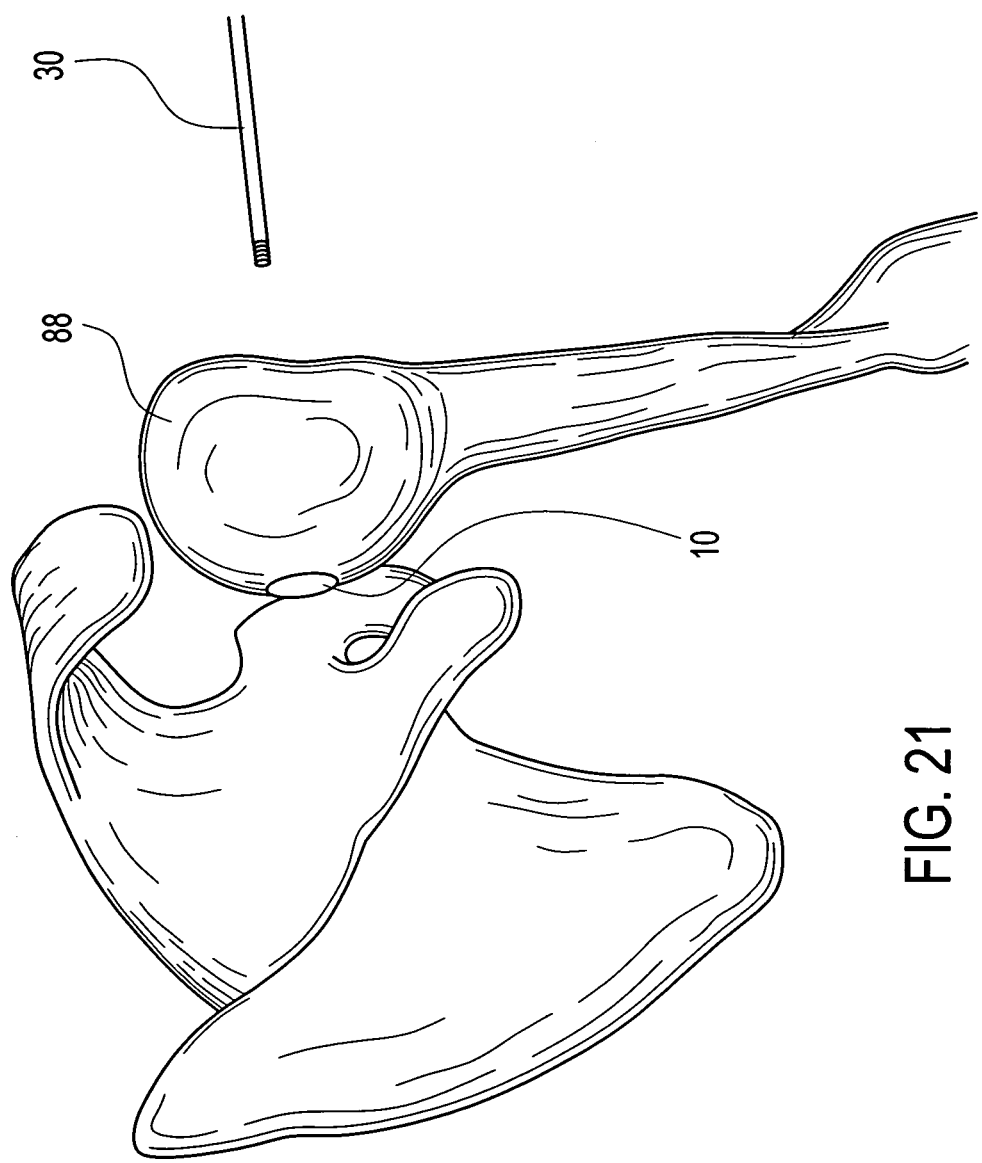

US 8,591,592 B2

METHOD OF IMPLANTING PARTIAL HUMERAL HEAD PROSTHESIS

CROSS-REFERENCE TO RELATED APPLICATIONS

This application claims the benefit of U.S. Provisional Application Ser. No. 60/915,280, filed May 1, 2007, the entire disclosure of which is incorporated by reference herein.

FIELD OF THE INVENTION

The present invention relates to surgical reconstitution of anatomical structures and, in particular, to prosthetic replacement of such structures.

BACKGROUND OF THE INVENTION

Instability and other maladies of human joints, such as arthrosis or fracture, can be sufficiently acute that prosthetic replacement of compromised joint features may be indicated. For example, in shoulder reconstruction, the humeral head may be replaced by first resecting the humeral head from the humerus and then installing a humeral prosthetic at the resection.

Various prostheses have been designed to mimic the portion of the joint or joint region being replaced. A shoulder prostheses, for example, includes a stem to be anchored in the humeral canal and a hemispherical head to be positioned within the glenoid cavity of the scapula. The more-recently devised modular shoulder prostheses generally are modular systems that allow flexibility with respect to either the tilt angle or the radial offset between the head and stem.

SUMMARY OF THE INVENTION

The present invention provides a novel prosthetic assembly for prosthetic and surgical methods for reconstitution of a joint, with special applications to the shoulder joint. The prosthetic assembly includes a partial humeral head component.

The present invention also provides a method of conducting surgery by providing a prosthetic assembly comprising a partial humeral head component fixed within a socket formed in the humerus.

These and other features and advantages of the invention will be more apparent from the following detailed description that is provided in connection with the accompanying drawings and illustrated exemplary embodiments of the invention.

BRIEF DESCRIPTION OF THE DRAWINGS

FIGS. 1-5 illustrate various views of a partial humeral head prosthesis according to a first embodiment of the present invention;

FIGS. 9-11 illustrate various views of a driver for the partial humeral head prosthesis of the present invention;

FIGS. 15-21 illustrate steps of a method of replacing a portion of the humeral head with the partial humeral head prosthesis of the present invention.

DETAILED DESCRIPTION OF THE PREFERRED EMBODIMENTS

Figure 2:
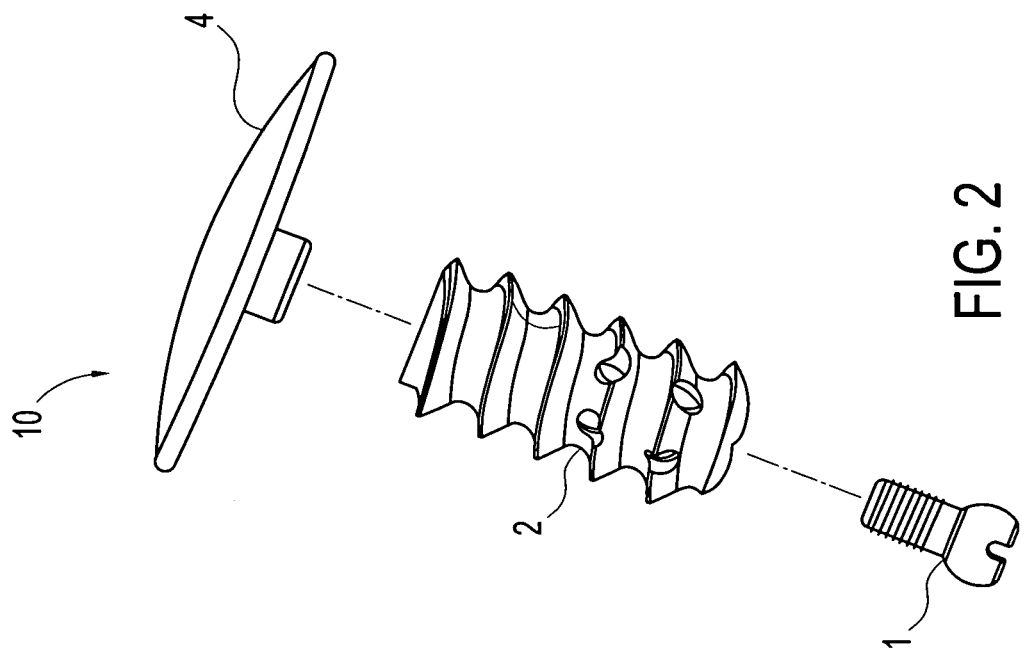
Figure 1:
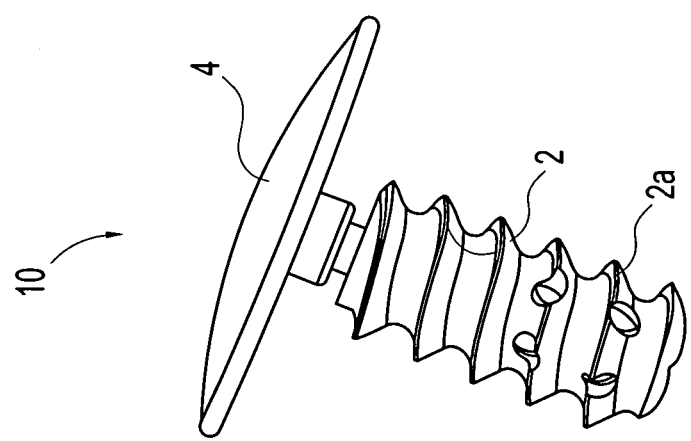

The invention provides prosthetic assembly for prosthetic and surgical methods for reconstitution of a joint, with special applications to the shoulder joint. As detailed below, the prosthetic assembly includes a partial humeral head prosthesis component that is configured to be inserted in a socket formed in the humerus.

Referring now to the drawings, where like elements are designated by like reference numerals, FIGS. 1-5 illustrate a first exemplary embodiment of a partial humeral head prosthesis 10 of the present invention. Partial humeral head prosthesis 10 comprises a partial humeral head prosthesis cap 4 securely engaged to a partial implant or screw 2 by shoulder post 1. FIGS. 3(a)-(e) illustrate additional views of the partial humeral head prosthesis implant or screw 2. FIGS. 4(a)-(c) illustrate additional views of the partial humeral head prosthesis cap 4. FIGS. 5(a)-(b) illustrate additional views of the shoulder post or pin 1.

As shown in the drawings, prosthesis cap 4 of the partial humeral head prosthesis 10 is configured to allow replacement of a portion of the humeral head with the prosthesis cap. In an exemplary embodiment, and as shown in FIGS. 4(a)-(c), partial humeral head prosthesis cap 4 has a convex configuration (a partial eclipse-type configuration), which is similar to the curvature of the humeral head to allow the prosthesis cap 4 to reconstruct the anatomy of the damaged humeral head. As described below, convex outer surface 4a (FIGS. 4(a)-4(c)) of the prosthesis cap 4 will permit both the full anatomical reconstruction of the humeral head and the introduction of the convex surface within the glenoid cavity. The concave, inner surface 4b (FIG. 4(a)) abuts the surface of the damaged articular bone to be replaced (i.e., portion of the humerus) and permits containment of any fractured, damaged humeral head. The dimension and measurements of the partial humeral head prosthesis cap 4 are a function of the patient's anatomy.

The partial humeral head prosthesis implant or screw 2 shown in FIGS. 3(a)-(e) is engaged to the prosthesis cap 4 through shoulder post or pin 1 shown in FIGS. 5(a)-(b). As detailed in FIGS. 3(a)-(e), implant or screw 2 is provided with threads 2a to allow the insertion and subsequent fixation of the screw (with prosthesis cap 4 attached thereto) into the humerus diaphyseal channel. A plurality of fenestrations or holes 2b formed through the body of the screw 2 permit the passage of any fixing material (such as acrylic cement, for example) through the walls of the screw 2, to increase the fixation of the device within the diaphyseal channel.

Partial humeral head prosthesis 10 may be manufactured from titanium alloy or other metallic materials. The partial humeral head prosthesis cap 4 preferably is manufactured from materials similar to those of the screw 2 and pin 1.

Figure 7:
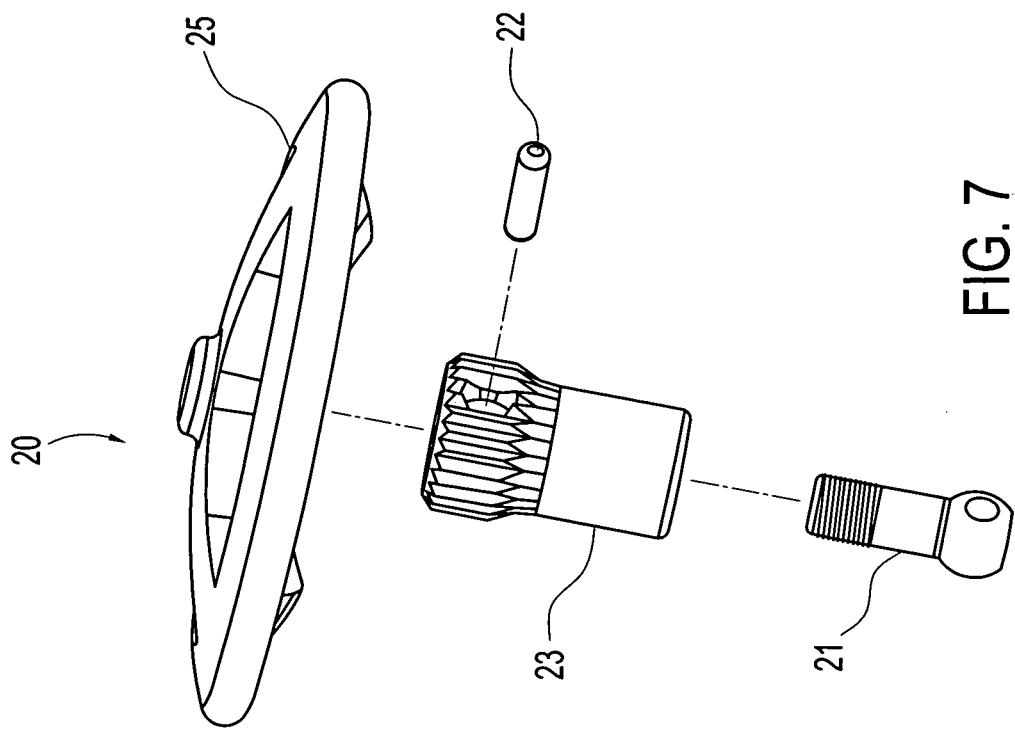
FIGS. 6-8 illustrate various views of a partial humeral head prosthesis articulating cutter of the present invention.
Figure 6:
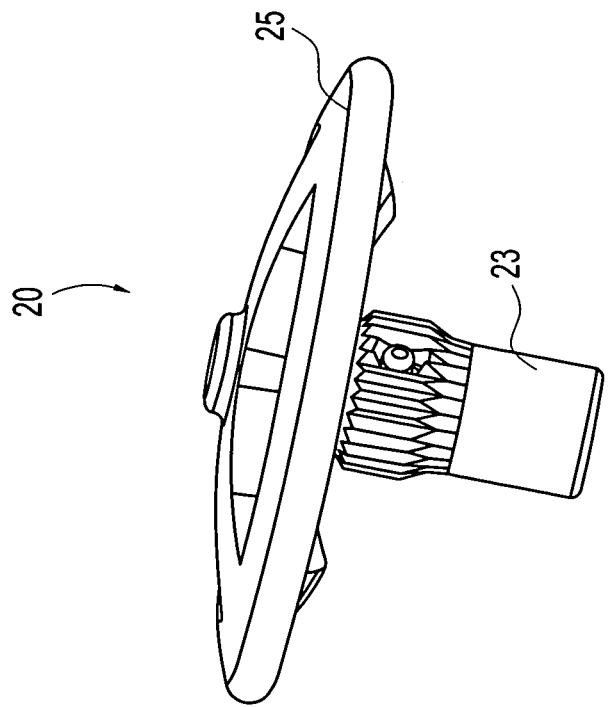
Figure 8:
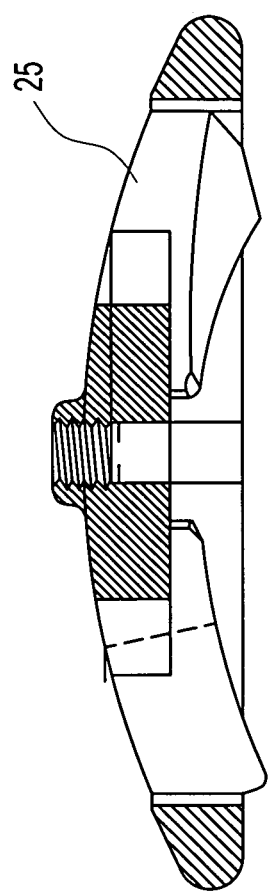

FIGS. 6-8 illustrate various views of partial humeral head prosthesis articulating cutter 20 of the present invention. As shown in the drawings, the partial humeral head prosthesis articulating cutter 20 comprises articulating cutter cap 25 securely engaging reamer 23 through ball post 21 and pin 22.

FIGS. 9-11 illustrate a driver 30 for the partial humeral head prosthesis 10 of the present invention. Driver 30 comprises an inner rod 33 disposed within a cannulated rod 34, and a handle 32. Driver 30 also comprises a spring driver 36, a spring plug 35 and ball bearings 31.

Figure 12:
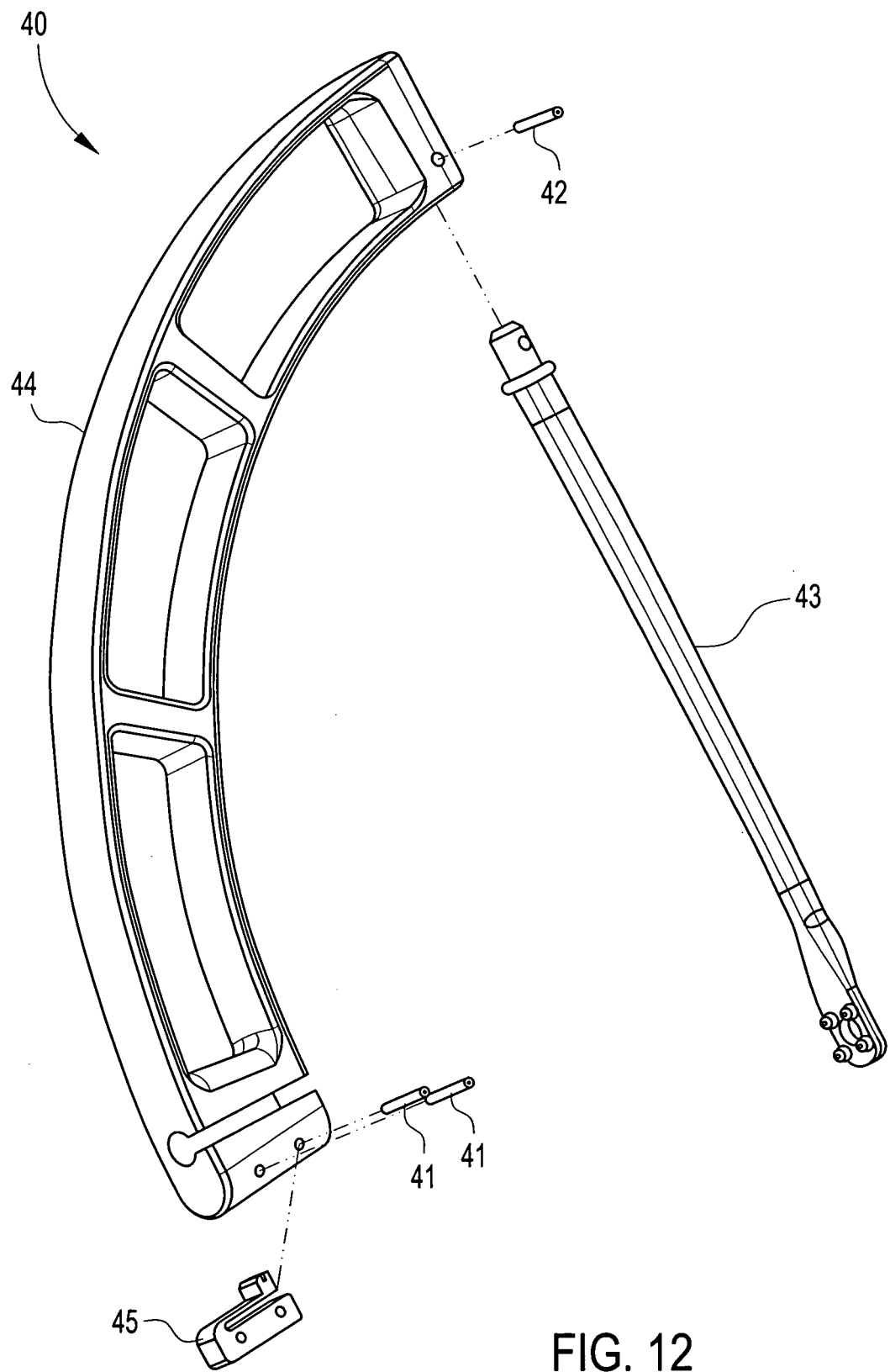
FIG. 12 illustrates a drill guide for installing the partial humeral head prosthesis of the present invention.

FIG. 12 illustrates a drill guide 40 for the partial humeral head prosthesis 10 of the present invention. Drill guide 40 comprises a handle frame 44, a guide arm 43, pins 41, 42 and spring latch 45.

Figure 13:
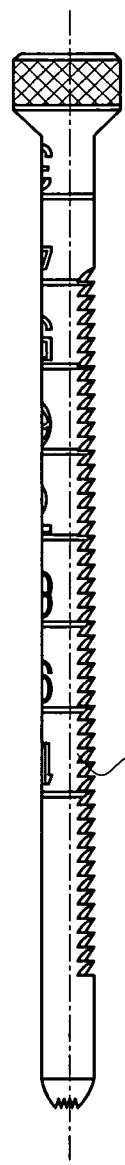
FIG. 13 illustrates a drill sleeve for use with the drill guide of the present invention.
Figure 14:
FIG. 14 illustrates various views of a pin for retrograde drilling of the duster of FIGS. 6-8 in connection with the present invention.

FIG. 13 shows a drill sleeve 50 for use with the drill guide 40 of FIG. 12 in connection with the present invention. FIG. 14 illustrates a threaded pin 60 for attachment to, and retrograde drilling of, articulating cutter 20 in connection with the present invention, as described in the technique below.

The present invention also provides a method of conducting arthroscopic surgery by fixating the humeral head prosthesis 10 of the present invention within a socket in the humerus. Preparation for an exemplary surgical technique relies upon radiographic film, surgical templates, and trial implants to determine and select the appropriate combination of end cap 4, screw 2 and pin 1 that make up partial humeral head prosthesis (implant) 10 to meet the patient's anatomical requirements. The remaining fractured/damaged humerus is resected using appropriate instrumentation designed specifically for the implant system.

Figure 15:
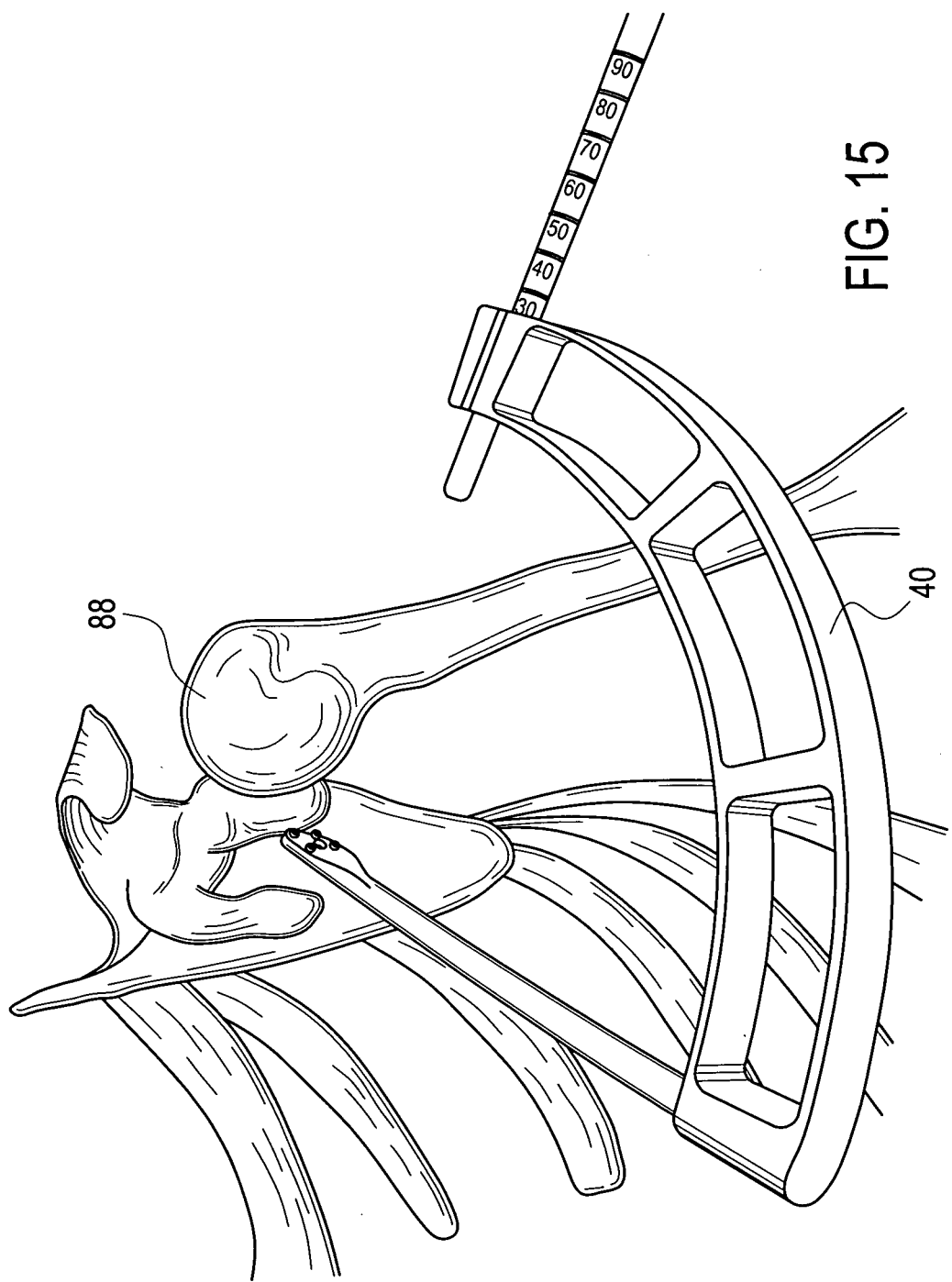
Figure 16:
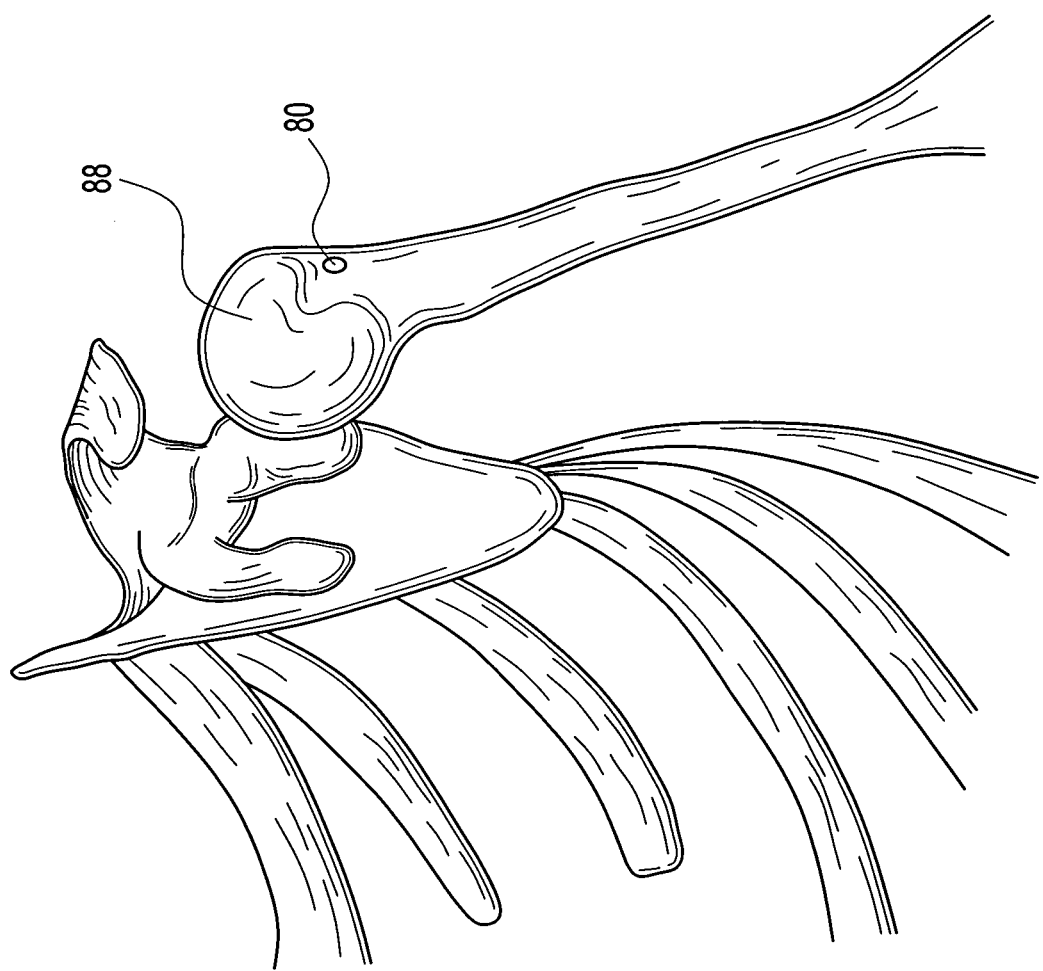
Figure 17:
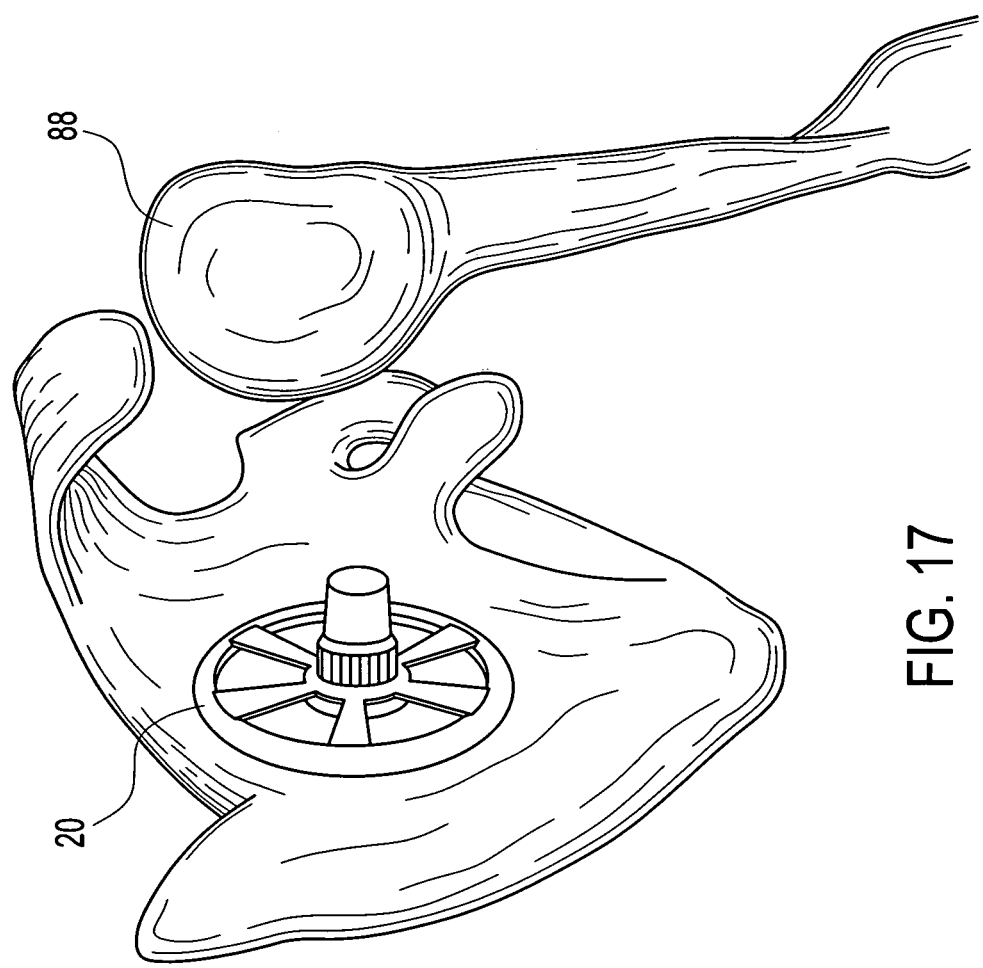

Specific steps of an exemplary method of humeral repair according to the present invention are detailed below and with reference to FIGS. 15-21 (which depict a method of replacing a portion of the humeral head with the partial humeral head prosthesis 10 of the present invention):

Use drill guide 40 with orthogonal orientation features to place 2.4 mm drill pin thru humeral head 88, exiting at center of focal defect (FIG. 15).

Remove drill guide 40, leaving the 2.4 mm drill pin in place.

Over-drill with 4 mm cannulated drill over 2.4 mm drill pin to form tunnel or hole 80 (FIG. 16) through the humerus 88, remove 4 mm drill leaving 2.4 mm drill pin in place.

Place sleeve component 50 over 2.4 mm drill pin, verifying whether sleeve 50 is in view with arthroscope. Remove 2.4 mm drill pin.

Insert threaded pin component 60 up sleeve 50 into view of arthroscope. Bring articulating cutter component 20 (FIG. 17), loaded onto insertion hand instrument, through rotator cuff interval portal into view. Assemble articulating cutter 20 to threaded pin 60 by hand.

Figure 18:
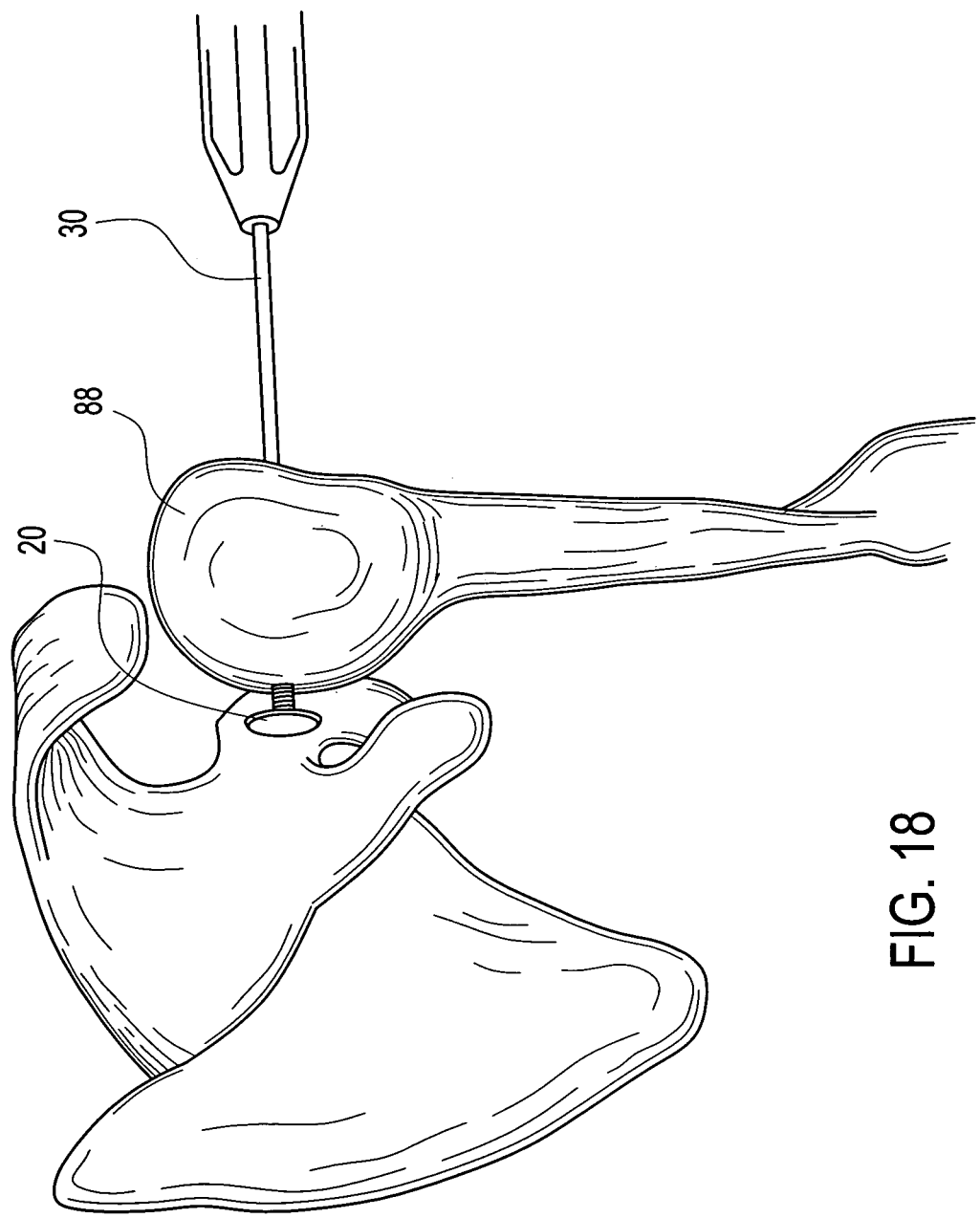

Load power drill onto threaded pin 60 and apply retrograde force while running drill to create a counterbore socket at focal defect location (FIG. 18).

Remove power drill. Grasp articulating cutter component 20 with insertion hand instrument and remove threaded pin 60, then remove articulating cutter component 20. Sleeve 50 should still be in place.

Figure 19:
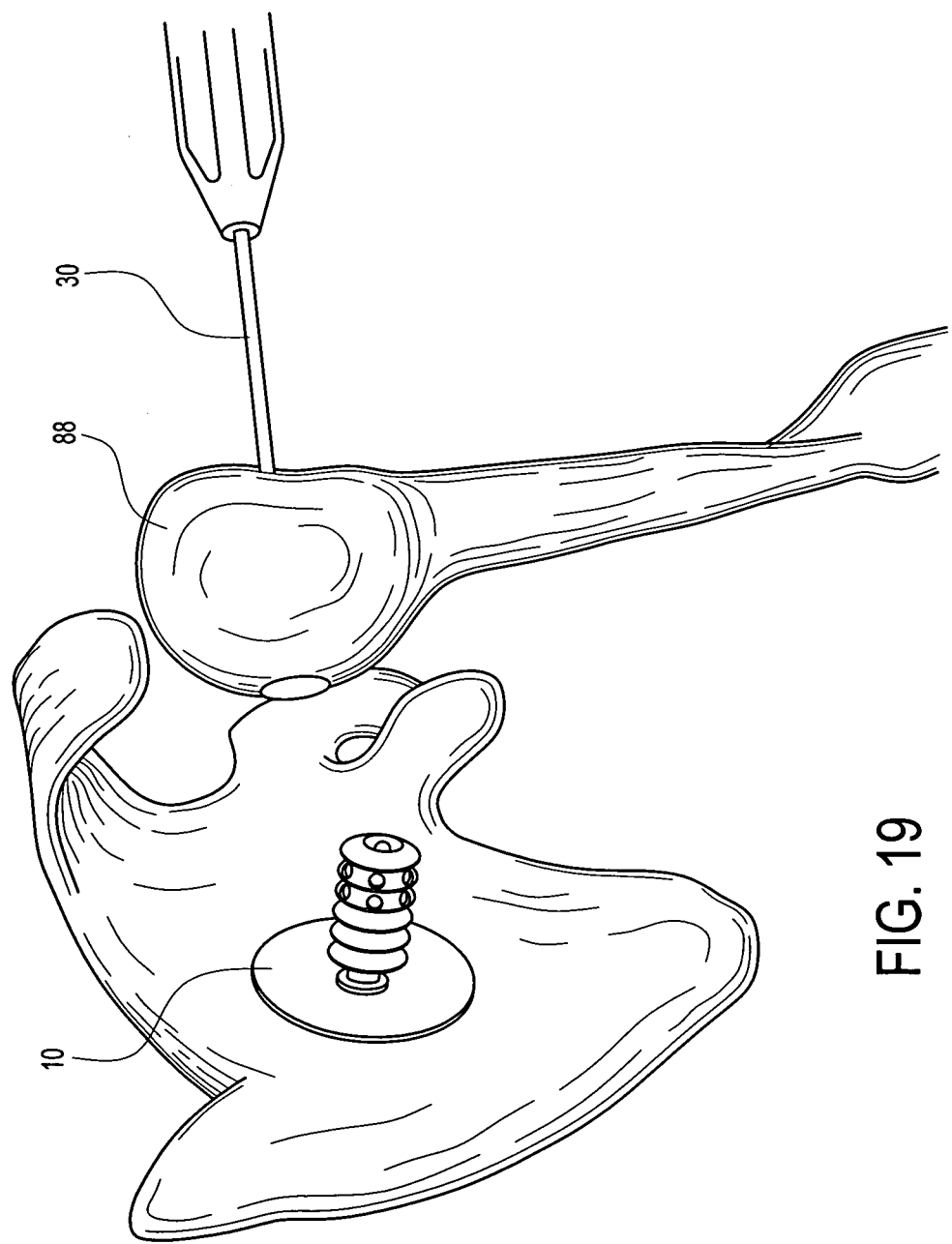

Insert implant inserter component 10 up sleeve into view of arthroscope. Bring implant 10, loaded onto insertion hand instrument, thru the rotator cuff interval portal into view (FIG. 19). Assemble implant 10 on inserter by hand.

Figure 20:
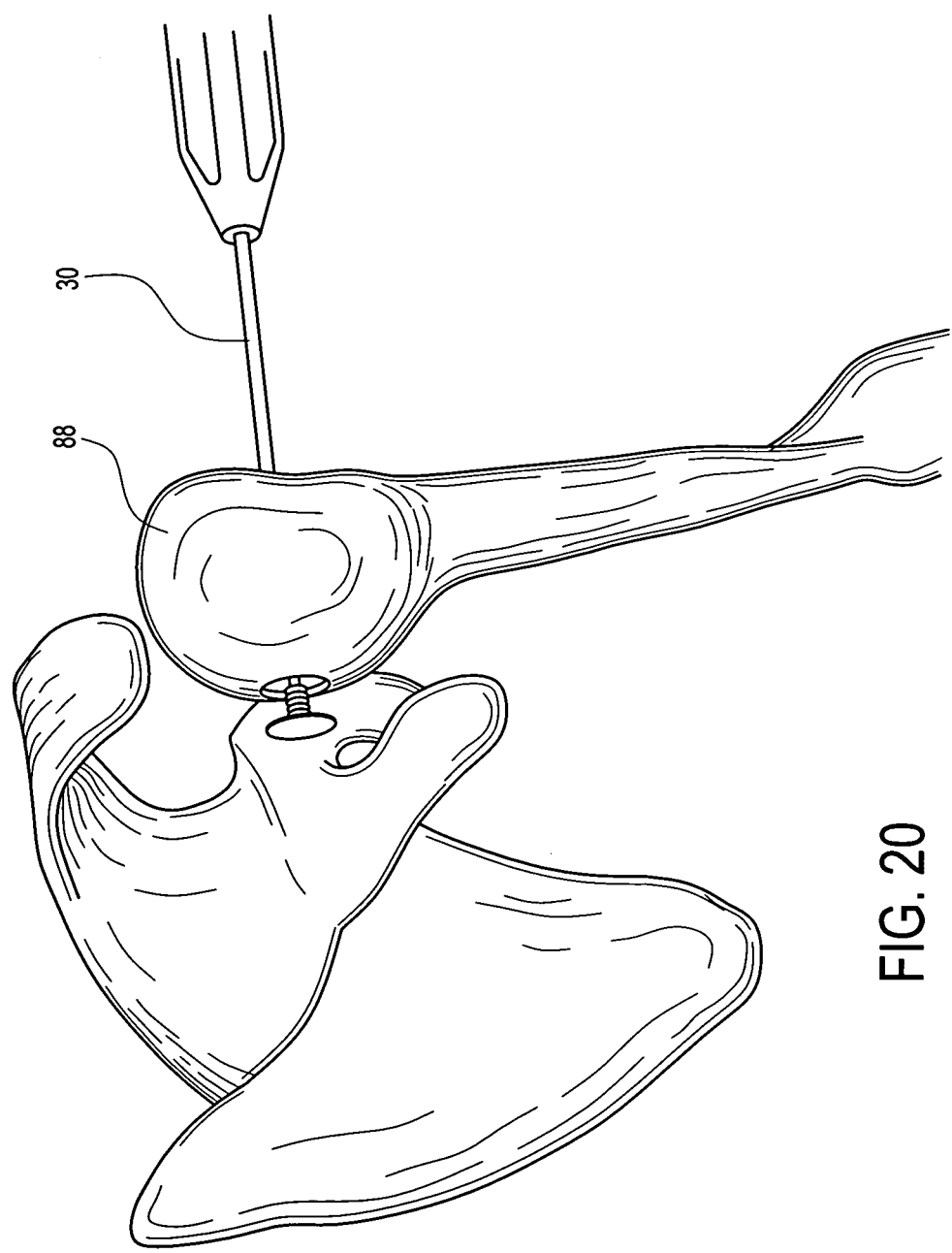

Retrograde insert implant 10 into the prepared socket until cap 4 of implant 10 is flush with the surrounding articular surface of the humerus (FIG. 20).

Remove the inserter, remove sleeve 50 and confirm that implant 10 is correctly installed (FIG. 21).

Figure 22A:
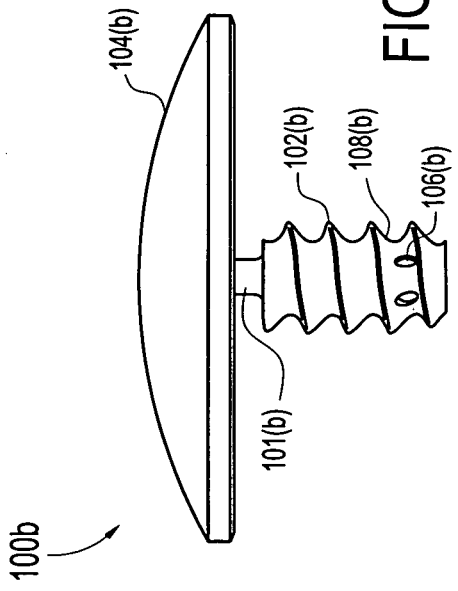
FIGS. 22 and 23 illustrate various views of a partial humeral head prosthesis according to a second embodiment of the present invention.
Figure 22B:
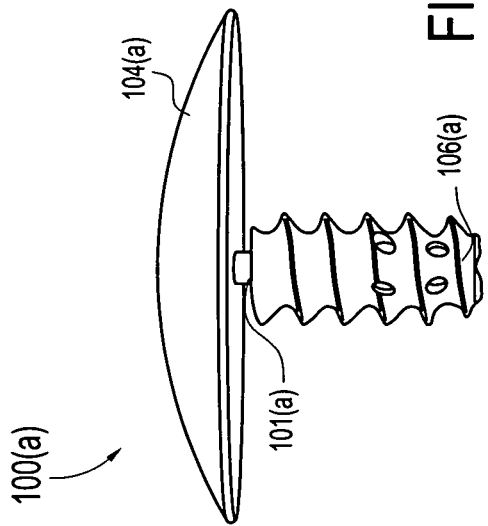
Figure 23A:
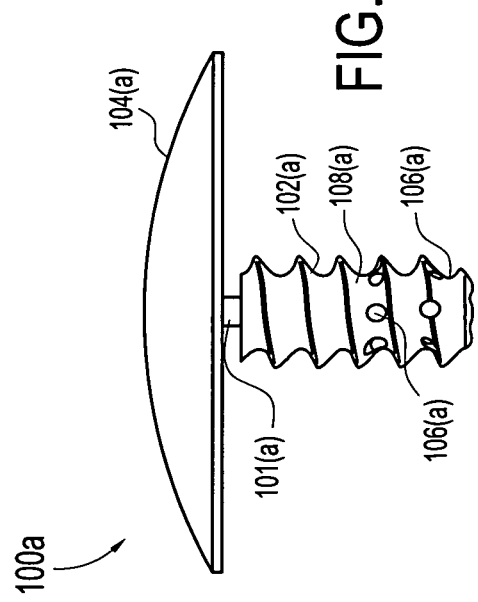
Figure 23B:
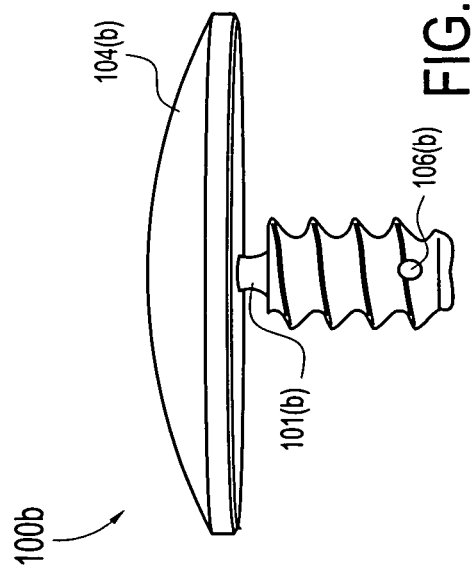

FIGS. 22 and 23 illustrate front and perspective views, respectively, of additional embodiments of a partial humeral head prosthesis 100(a), 100(b) formed according to a second embodiment of the present invention. Partial humeral head prosthesis 100(a), 100(b) is similar to the partial humeral head prosthesis 10 described above, but differs in that humeral head prosthesis 100(a), 100(b) is formed as a unitary structure rather than as an assembled structure (i.e., a partial humeral head prosthesis cap is integral to a partial implant or screw, and not assembled to it). Partial humeral head prosthesis 100(a), 100(b) comprises a partial humeral head prosthesis cap 104(a), 104(b) securely attached to, and integral with, a partial implant or screw 102(a), 102(b).

As shown in FIGS. 22 and 23, prosthesis cap 104(a), 104(b) is configured to allow replacement of a portion of the humeral head with the prosthesis cap. As in the previously-described embodiment, partial humeral head prosthesis cap 104(a), 104(b) has a convex configuration (a partial eclipse-type configuration), which is similar to the curvature of the humeral head to allow the prosthesis cap to reconstruct the anatomy of the damaged humeral head. The convex outer surface of the prosthesis cap 104(a), 104(b) permits both the full anatomical reconstruction of the humeral head and the introduction of the convex surface within the glenoid cavity. The concave, inner surface abuts the surface of the damaged articular bone to be replaced (i.e., portion of the humerus) and permits containment of any fractured, damaged humeral head. The dimension and measurements of the partial humeral head prosthesis cap 104(a), 104(b) are a function of the patient's anatomy.

Engagement element (neck portion) 101(a), 101(b) is provided between the partial humeral head prosthesis implant or screw 102(a), 102(b) and the prosthesis cap 104(a), 104(b). Implant or screw 102(a), 102(b) is provided with threads 108(a), 108(b) to allow the insertion and subsequent fixation of the screw (with prosthesis cap attached thereto) into the humerus diaphyseal channel. As shown in FIGS. 22 and 23, the length of the implant 102(a), 102(b) varies according to the length of the diaphyseal channel of the humerus.

A plurality of fenestrations or holes 106(a), 106(b) are formed through the body of the screw 102(a), 102(b) to permit the passage of any fixing material (such as acrylic cement, for example) through the walls of the screw, to increase the fixation of the device within the diaphyseal channel. The number of the fenestrations or holes 106(a), 106(b) depends on the length of the implant 102(a), 102(b) and also on the length of the diaphyseal channel of the humerus.

Partial humeral head prosthesis 100(a), 100(b) may be manufactured from titanium alloy or other metallic materials. The partial humeral head prosthesis cap 104(a), 104(b) preferably is manufactured from materials similar to those of the screw 102(a), 102(b).

Methods of conducting arthroscopic surgery by fixating the humeral head prosthesis 100(a), 100(b) within a socket in the humerus may be conducted by steps similar to those described and illustrated above with reference to humeral head prosthesis 10 of the first embodiment (for the humeral repair illustrated in FIGS. 15-21). Selection of the appropriate size for the partial humeral head prosthesis (implant) 100(a), 100(b) is based on the patient's anatomical requirements. The specific steps proceed as detailed above and with reference to FIGS. 15-21.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A method of shoulder repair, comprising the steps of:
   providing a humeral prosthetic comprising a spherical head having a convex surface suitable to be introduced within a joint cavity and a concave surface that is adapted to contact a humerus;

providing a portal through the rotator cuff interval;

forming a tunnel in the humerus at a defect location within the humerus;

providing an articulating cutter comprising a cap and a reamer, the cap securely engaging the reamer through a ball joint with cross-pin fixation formed of a ball post and a pin that limits rotation but allows the cutter to articulate;

inserting the articulating cutter through the rotator cuff interval portal;

assembling the articulating cutter with a threaded pin and applying retrograde force while the articulating cutter cuts in a retrograde manner and through the preformed tunnel in the humerus to form a counterbore socket until the articulating cutter is flush with an articular surface of the humerus;

removing the articulating cutter and the threaded pin; and installing the humeral prosthetic within the counterbore socket in the humerus.

2. The method of claim 1, wherein the spherical head further comprises a cylindrical stem portion extending about perpendicular to the convex surface, and wherein the humeral prosthetic further comprises the cannulated member attachable to the cylindrical stem portion of the spherical head, the cannulated member being insertable within the tunnel in the humerus; and a post configured to secure the cannulated member to the spherical head, wherein the cannulated member is a cannulated screw.

3. The method of claim 2, wherein the cannulated screw is threaded.

4. The method of claim 2, wherein the cannulated screw is provided with a plurality of fenestrations.

5. The method of claim 2, wherein at least a portion of an internal cylindrical stem area of the cylindrical stem portion of the head is threaded, and wherein the post has a body with at least a threaded region that corresponds to the threaded internal stem area of the head when the cannulated member is attached to the head.

6. The method of claim 1, wherein the humeral prosthetic is installed within the counterbore socket in the humerus using a driver, by attaching a cannulated member of the humeral prosthetic with the spherical head of the prosthetic to the driver inside the joint cavity, the driver being inserted into the joint cavity through the preformed tunnel in the humerus, and installing the prosthetic, in retrograde fashion and through the portal through the rotator cuff interval, into the humerus, using the driver until the spherical head is flush with the articular surface of the humerus.

* * * * *